(12) United States Patent
Peery

(10) Patent No.: US 7,063,681 B1
(45) Date of Patent: Jun. 20, 2006

(54) TROCAR FOR INSERTING IMPLANTS

(75) Inventor: John R. Peery, Stanford, CA (US)

(73) Assignee: Alza Corporation, Palo Alto, CA (US)

( * ) Notice: Subject to any disclaimer, the term of this patent is extended or adjusted under 35 U.S.C. 154(b) by 0 days.

(21) Appl. No.: 09/296,582

(22) Filed: Apr. 23, 1999

Related U.S. Application Data

(60) Provisional application No. 60/082,759, filed on Apr. 23, 1998.

(51) Int. Cl.
A61M 31/00 (2006.01)

(52) U.S. Cl. ............... 604/60; 604/164.01; 606/117; 600/7

(58) Field of Classification Search .......... 604/57, 604/ 59–64, 164.01, 264, 272, 273, 274, 604/ 239, 164.11, 164.12, 170.01, 170.02, 604/ 187, 218, 506; 606/1, 117, 116, 107, 606/ 187; 600/1, 3, 7, 8
See application file for complete search history.

(56) References Cited

U.S. PATENT DOCUMENTS

| | | | | |
|---|---|---|---|---|
| 421,072 | A | * | 2/1890 | Harris ............... 604/59 |
| 1,655,158 | A | * | 1/1928 | Muir ................. 29/39 |
| 2,587,364 | A | | 2/1952 | Mitchell |
| 2,751,907 | A | | 6/1956 | Hickey |
| 2,904,045 | A | | 9/1959 | Owings |
| 3,667,465 | A | | 6/1972 | Voss |
| 4,060,083 | A | | 11/1977 | Hanson |
| 4,077,406 | A | * | 3/1978 | Sandhage et al. ...... 128/217 |
| 4,105,030 | A | * | 8/1978 | Kercso ............... 604/506 |
| 4,111,202 | A | | 9/1978 | Theeuwes |
| 4,111,203 | A | | 9/1978 | Theeuwes |
| 4,147,164 | A | | 4/1979 | Behney |
| 4,155,125 | A | | 5/1979 | Woodcock et al. |
| 4,203,439 | A | | 5/1980 | Theeuwes |
| 4,329,985 | A | | 5/1982 | Bonchek |
| 4,490,139 | A | | 12/1984 | Huizenga et al. |
| 4,565,545 | A | * | 1/1986 | Suzuki ............... 604/164 |
| 4,700,692 | A | | 10/1987 | Baumgartner |
| 4,708,147 | A | | 11/1987 | Haaga |
| 4,787,384 | A | * | 11/1988 | Campbell et al. ...... 128/330 |
| 4,919,322 | A | | 4/1990 | Fortune et al. |
| 4,919,678 | A | | 4/1990 | Kranz |

(Continued)

FOREIGN PATENT DOCUMENTS

| | | | |
|---|---|---|---|
| AU | 288070 A | * | 11/1967 |
| AU | 64855/94 | | 1/1995 |
| EP | 0 537 955 | | 4/1993 |
| EP | 0 631 794 | | 1/1995 |
| EP | 0 639 387 A | | 2/1995 |
| EP | 0 639 387 A1 | * | 2/1995 |
| EP | 0 739 639 A | | 10/1996 |
| EP | 0 819 442 A | | 1/1998 |
| FR | 1225009 | | 6/1960 |
| FR | 1225099 A | | 6/1960 |
| GB | 1453698 A | | 10/1976 |
| GB | 2199247 | | 7/1988 |
| WO | WO 94/04082 | | 3/1994 |
| WO | WO 96/01104 | | 1/1996 |
| WO | 97/22379 A | | 6/1997 |

*Primary Examiner*—Brian Casler
*Assistant Examiner*—Jennifer Maynard
(74) *Attorney, Agent, or Firm*—TraskBritt

(57) ABSTRACT

An implant retention trocar includes a cannula for puncturing the skin of an animal and an obturator for delivering the implant beneath the skin of the animal. The implant retention trocar has a cannula distal tip design which causes a minimum of trama and tearing of tissue during implant insertion. A spring element received within the cannula prevents an implant which is to be inserted into an animal from falling out of the cannula during the implant insertion process. The spring element includes a longitudinal leg which is folded with a zig-zag shaped bend. When the spring element is inserted into the cannula the zig-zag shaped bend of the longitudinal leg retains the implant within the cannula.

15 Claims, 4 Drawing Sheets

U.S. PATENT DOCUMENTS

| | | |
|---|---|---|
| 4,931,042 A | 6/1990 | Holmes et al. |
| 5,122,122 A | 6/1992 | Allgood |
| 5,169,602 A | 12/1992 | Pang et al. |
| 5,273,532 A | 12/1993 | Niezink et al. |
| 5,279,593 A | 1/1994 | Hiltebrandt |
| 5,295,993 A | 3/1994 | Green |
| 5,356,381 A * | 10/1994 | Ensminger et al. ........... 604/93 |
| 5,368,045 A | 11/1994 | Clement et al. |
| 5,380,305 A | 1/1995 | Ghouri |
| 5,383,882 A | 1/1995 | Buess et al. |
| 5,385,151 A | 1/1995 | Scarfone et al. |
| 5,400,798 A | 3/1995 | Baran |
| 5,407,431 A | 4/1995 | Botich et al. |
| 5,484,422 A | 1/1996 | Sloane, Jr. et al. |
| 5,486,190 A | 1/1996 | Green |
| 5,492,130 A | 2/1996 | Chiou |
| 5,520,660 A * | 5/1996 | Loos et al. .................. 604/236 |
| 5,536,259 A * | 7/1996 | Utterberg ..................... 604/272 |
| 5,669,890 A | 9/1997 | Grimm |
| 5,672,357 A | 9/1997 | Baile et al. |
| 5,733,266 A | 3/1998 | Gravlee, Jr. |
| 5,752,942 A | 5/1998 | Doyle et al. |
| 5,772,671 A * | 6/1998 | Harmon ...................... 606/117 |
| 5,810,769 A * | 9/1998 | Schlegel et al. ............... 604/59 |
| 5,831,743 A | 11/1998 | Ramos et al. |
| 5,876,384 A | 3/1999 | Dragan et al. |
| 6,070,501 A | 6/2000 | Braun et al. |
| 6,190,350 B1 | 2/2001 | Davis et al. |
| 6,450,938 B1 | 9/2002 | Miller |

* cited by examiner

TROCAR FOR INSERTING IMPLANTS

This application claims priority based on U.S. Provisional Application No. 60/082,759 filed Apr. 23, 1998, which is incorporated herein by reference in its entirety.

FIELD OF THE INVENTION

The invention relates to a tubular member for inserting drug-containing devices into animals and more particularly, the invention relates to a trocar for inserting implants.

BACKGROUND OF THE INVENTION

Many different types of delivery systems for delivering beneficial agents such as pharmaceuticals for the prevention, treatment, and diagnosis of disease are known in the art. One type of delivery system is the subcutaneous implant which contains a supply of a beneficial agent and is implanted beneath the skin of an animal to deliver the beneficial agent over time. Some of the different types of subcutaneous implants include osmotic drug delivery implants, dissolvable or erodable pellet type implants, and diffusional implants. Some examples of osmotic delivery implant systems are described in U.S. Pat. Nos. 4,111,202; 4,111,203; and 4,203,439.

The process of placing subcutaneous osmotic implants and other types of implants under the skin is often performed by use of a trocar system which is a two-piece system, including a cannula and an obturator. With this system, an incision is first made through the skin of the patient and the cannula and obturator are inserted together through the skin. The obturator is then withdrawn leaving the cannula in place as a guide for inserting the implant. The implant is inserted through the bore of the cannula while the obturator is used to push the implant to the end of the cannula. The obturator is then used to hold the implant in a stable axial position while the cannula is being withdrawn from the patient to deposit the implant in a known position in the channel previously occupied by the cannula. The cannula and obturator are then withdrawn completely leaving the implant in place beneath the skin.

This method of insertion of an implant, including the step of removal of the obturator for insertion of the implant through the cannula followed by reinsertion of the obturator increases the possibility that sterility of the implant site will be compromised during these steps. However, it is difficult to insert the implant into the cannula prior to insertion of the cannula into the patient because the implant will tend to fail out of the cannula during the insertion process.

Known trocars can also be used with the implant in the trocar during insertion, however this method relies upon the skilled and careful use by the health care practitioner to orient the trocar so as to employ gravity to retain the implant in the cannula. Alternatively, implants capable of distortion may be held in a cannula by interference with a wall of the cannula to keep the implant in place against the force of gravity.

Known balling guns have been used in veterinary implantation procedures which retain the implant or bolus tablet in a cannula by either an interference fit or a distortion of the cannula. However, the cannulas are generally complex and expensive to manufacture.

Accordingly, it would be desirable to provide a trocar system in which an implant may be retained within the cannula in a simple and economical manner during insertion of the cannula into a patient and the implant is easily pushed out of the cannula and into the patient.

SUMMARY OF THE INVENTION

The trocar system according to a preferred embodiment of the present invention includes a cannula retaining spring element which is fixed to an inside surface of the cannula to retain an implant within the cannula until the implant is to be delivered by pressure applied by an obturator.

According to one aspect of the present invention, a trocar includes a cannula for receiving an implant and inserting the implant into an animal, a spring element received within the cannula, and an obturator for delivering the implant from the cannula into the animal. The spring element has a leaf spring for retaining the implant inside the cannula. The leaf spring applies a frictional force against the implant sufficient to prevent the implant from sliding out of the cannula under the weight of the implant.

In accordance with an additional aspect of the invention, a trocar includes a substantially cylindrical cannula body, a distal end of the cannula body having a leading edge formed by a first plane which is at a first angle with respect to a longitudinal access of the cannula body, and a trailing edge formed by a second plane which is at a second angle with respect to the longitudinal access of the cannula body. The first angle of the leading edge is larger than the second angle of the trailing edge.

BRIEF DESCRIPTION OF THE DRAWINGS

The invention will be described in greater detail with reference to the accompanying drawings, in which like elements bear like reference numerals, and wherein.

DETAILED DESCRIPTION OF THE PREFERRED EMBODIMENTS

The implant retention trocar according to the present invention includes a cannula and an obturator for implanting beneficial agent delivery devices in animals. According to one embodiment the cannula may be used to puncture a foil or other covering material of a sterile sealed implant package. Alternatively, the implant package may be opened by screwing, tearing, or cutting. The cannula then may be used to remove the implant from the package or the implant may be placed in the cannula by hand or with forceps. The implant is delivered to an implantation site within an animal, generally just beneath the skin, by the trocar by applying pressure to the obturator. The implant retention trocar causes a minimum of trauma and tearing of tissue during implant insertion.

A first aspect of the invention relates to a spring element 10 received within the cannula of the trocar to prevent an implant which is to be inserted into an animal from falling out of the cannula during the implant insertion process. Another aspect of the invention relates to the shape of the distal end of the cannula which prevents trauma and tearing of tissue during implant insertion.

Figure 1:
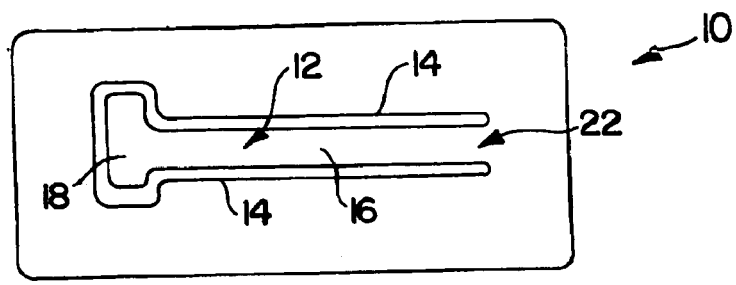
FIG. 1 is a top view of a spring element according to the present invention prior to bending of the leaf spring.
Figure 2:
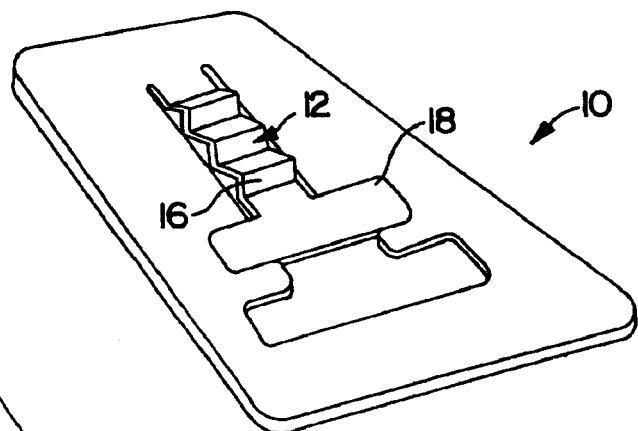
FIG. 2 is a perspective view of the spring element of FIG. 1 with the leaf spring bent.
Figure 3:
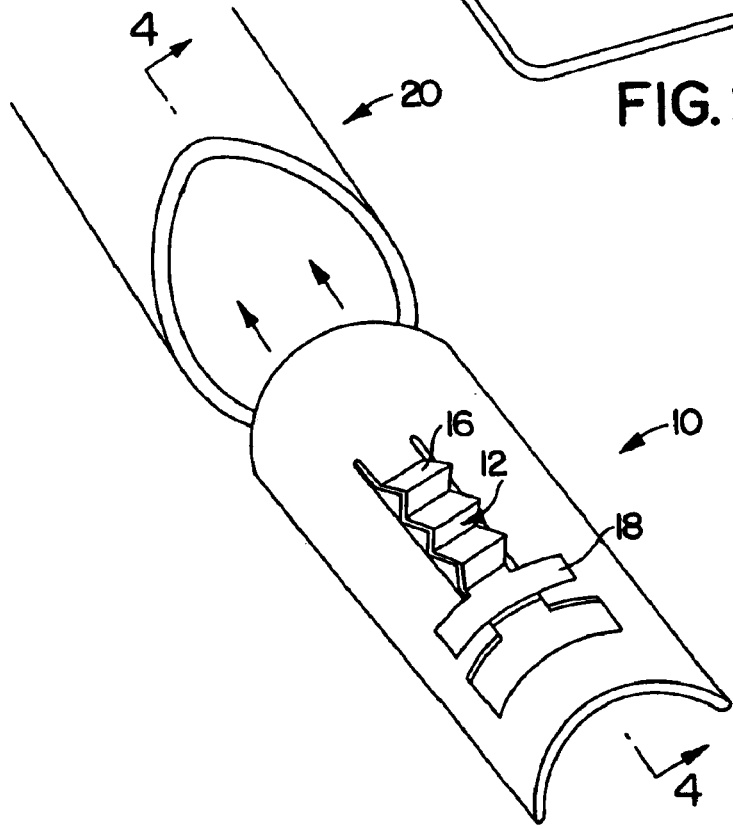
FIG. 3 is a perspective view of the spring element of FIGS. 1 and 2 which has been bent in an arch for insertion into a cannula.

The spring element 10 is shown in a finished configuration in FIG. 3 as it is inserted into a cannula 20. The spring element will be described with respect to FIGS. 1–3 according to the steps by which the spring element is formed. As shown in FIG. 1, the spring element is formed from a thin sheet of metal, such as a stainless steel, titanium, aluminum, copper, or other appropriate spring metal. The sheet is substantially rectangular in shape with a continuous cut 14 forming a T-shaped leaf spring 12. The cut 14 may be made in any known manner such as by punching or photoetching. The leaf spring portion 12 of the spring element 10 has a longitudinal leg 16 and a cross leg 18 extending substantially perpendicular to the longitudinal leg. The spring element 10 may be punched, photoetched, laser cut, or formed in any other known method.

As shown in FIG. 2, the longitudinal leg 16 is folded with a zig-zag shaped bend. When the spring element 10 is inserted into a cannula it is the zig-zag shaped bend of the longitudinal leg 16 which will retain the implant within the cannula. The cross leg 18 of the leaf spring 12 is wider than the longitudinal leg 16 in the circumferential direction and provides tabs on either end which 25 secures the leaf spring against motion away from the cannula surface toward the cannula axis. Bending of the longitudinal leg 16 in the zig-zag shape has the effect of shortening the distance from the cross leg 18 to an attachment point 22 where the longitudinal leg meets the rest of the spring element. Once shortened, end portions or tabs of the cross leg 18 lie along the surface of the spring element plate guiding the bent longitudinal leg. The cross leg 18 is slidable in a direction parallel to the cannula axis along the cylindrical surface of the cannula as the zig-zag shaped longitudinal leg 16 is extended and retracted. The ends of the cross leg 18 keep the longitudinal leg 16 properly oriented so that the longitudinal leg does not block loading of the implant into the cannula. The number and angle of the bends in the longitudinal leg 16 may be varied as needed to achieve implant retention.

FIG. 3 illustrates the spring element 10 once it has been bent about a longitudinal axis into an arch shape for insertion into the cannula 20. The radius of curvature of the arched spring element 10 is preferably approximately the same as or slightly smaller than a radius of the cannula 20 in which the spring element will be inserted. Once the spring element 10 is placed within the cannula 20, the spring element is preferably fixed inside the cannula by a sterilizable adhesive, such as cyanoacrylate, epoxy, polyester, acrylic, or other adhesive. The adhesive is preferably both biocompatible and compatible with the beneficial agent inside the implant to be delivered by the trocar. The spring element 10 may also be fixed inside the cannula by other known methods such as welding, laser welding, electric resistance welding, or the like.

Figure 4:
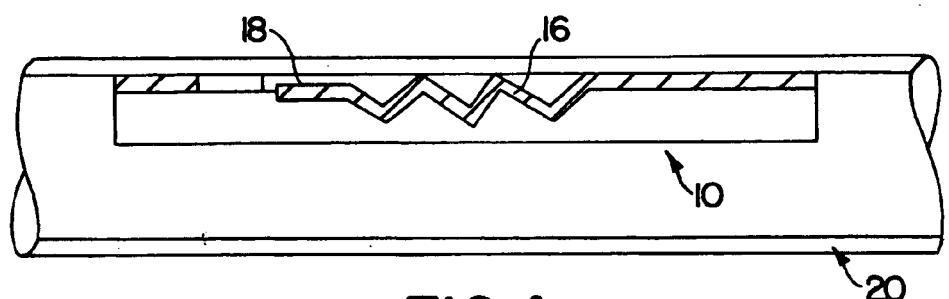
FIG. 4 is a cross-sectional side view of a portion of a cannula of FIG. 3, taken along line 4—4, with the spring element according to the present invention inserted within the cannula.
Figure 5:
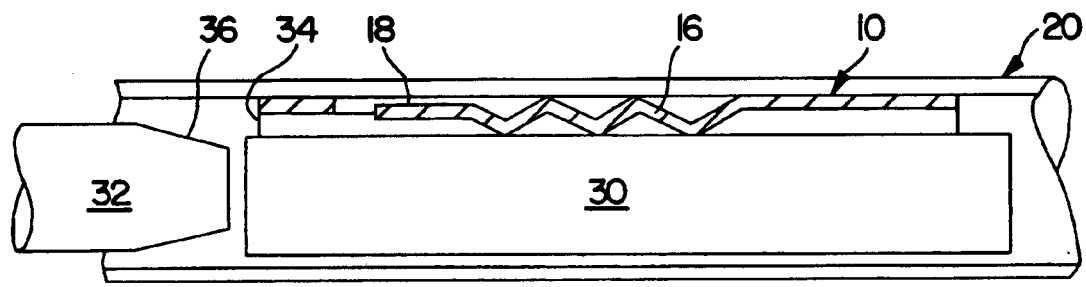
FIG. 5 is a side cross-sectional view of the cannula and leaf spring element of FIG. 4 with an implant and obturator inserted in the cannula.

Once the spring element 10 has been fixed within the tip of the cannula 20 and an implant has been inserted into the cannula, the zig-zag configuration of the longitudinal leg 16 exerts a force between an external surface of the implant and an internal surface of the cannula to retain the implant in the cannula until it is expelled by axial sliding of the obturator by the user. Cross sectional views of the cannula 20 and spring element 10 are shown in FIGS. 4 and 5 with and without an implant 30 and obturator 32. As can be seen from the figures, the amount of bend of the longitudinal leg 16 is decreased by the insertion of the implant causing the implant to be retained in the cannula by the spring retention force of the longitudinal leg.

FIG. 5 illustrates a distal end of an obturator 32 according to the present invention having a tapered exterior end surface 36 to prevent the spring element 10 from being expelled by motion of the obturator. In particular, the distal end of the obturator has a frusto-conical shape which prevents the obturator from becoming caught on either the edge 34 of the spring element 10 or on the edge of the cross leg 18.

Although the spring element 10 has been described as formed of a metal material, the spring element may also be formed of another spring material such as plastic, in the shape described above. The spring element 10 may be formed of plastic by molding, extruding, cold forming, thermo forming or a combination of these processes. In addition, the shape of the leaf spring 12 can be modified without departing from the invention. For example, the cross leg 18 of the leaf spring can be formed in any shape as long as it is somewhat larger in width than the longitudinal leg 16. The longitudinal leg 16 may also take on other shapes such as a tapered shape, as long as the leg has sufficient length form the formation of one or more bends.

The spring element 10 according to the present invention retains the implant within the cannula without requiring the grinding of special retention features into the cannula inner wall which would require expensive secondary operations. The retention spring element 10 according to the invention can be produced economically by punching, photoetching, or laser cutting and can be inserted in an automated fashion. Thus, the implant retention trocar can be inexpensively produced as a single-use device formed of recyclable materials.

Figure 6:
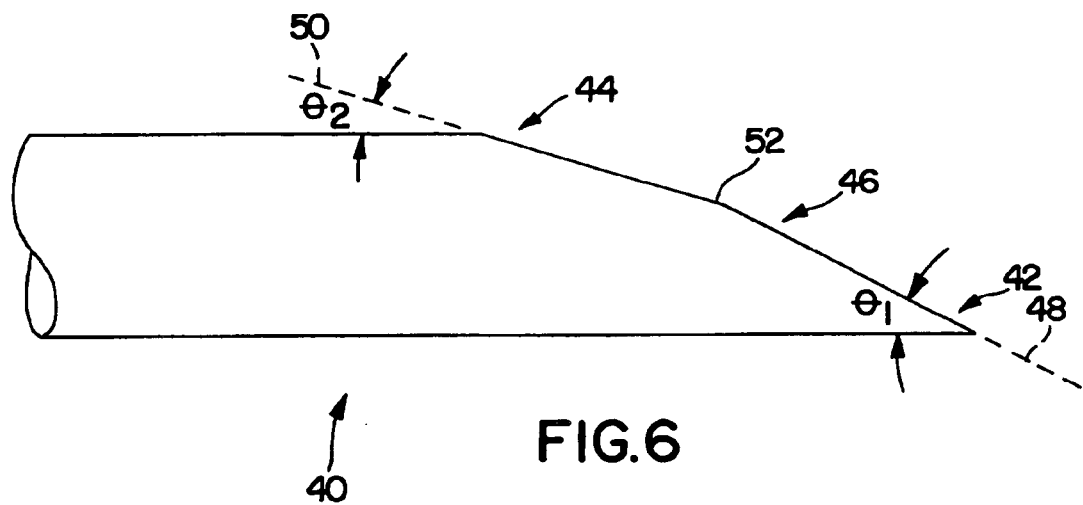
FIG. 6 is a side view of a first embodiment of the cannula tip.

The preferred embodiments of the cannula tip illustrated in FIGS. 6–11 in combination with the spring element described above provide an improved, easy to use and economical trocar. The cannula tip 40 shown in FIG. 6 includes a distal end having a changing profile between a leading edge 42 and a trailing edge 44 of the distal end opening 46 of the cannula. In particular, when viewed in profile, as shown in FIG. 6, the distal end of the cannula is cut by a first plane 48 and by a second plane 50. The first plane 48 forms an angle $\theta_1$ with a longitudinal axis of the cannula and the second plane 50 forms and angle $\theta_2$ with the longitudinal axis. The angle $\theta_1$ is about 10 to 60 degrees, preferably 20 to 40 degrees, and the angle $\theta_2$ is about 5 to 45 degrees, preferably 5 to 25 degrees. A difference between the angles $\theta_1$ and $\theta_2$ is between about 2 and 50 degrees, preferably between about 6 and 35 degrees.

A transition section 52 of the cannula distal end between the first plane 48 and the second plane 50 is preferably a gradual or blended transition rather than an abrupt transition. A gradual transition according to the present invention may be a slight rounding just at the intersection between the first and second planes. Alternatively, the gradual transition may include a curved surface extending along up to about one third of the distal end opening. This transition section 52 is located within either a central or top third of the cannula between the top and bottom of the cannula. The transition section provides a slight protruding bump which assists in spreading tissue during cannula insertion.

The two different angles $\theta_1$, and $\theta_2$ at the distal end of the cannula according to the present invention provide reduced tissue trauma and tearing during the trocar insertion. In particular, the relatively shallow angle at the trailing edge 44 of the cannula 40 avoids coring or tearing tissue during insertion of the cannula and also avoids coring when the cannula is used to puncture it's own foil packaging or the packaging of an implant.

Figure 7:
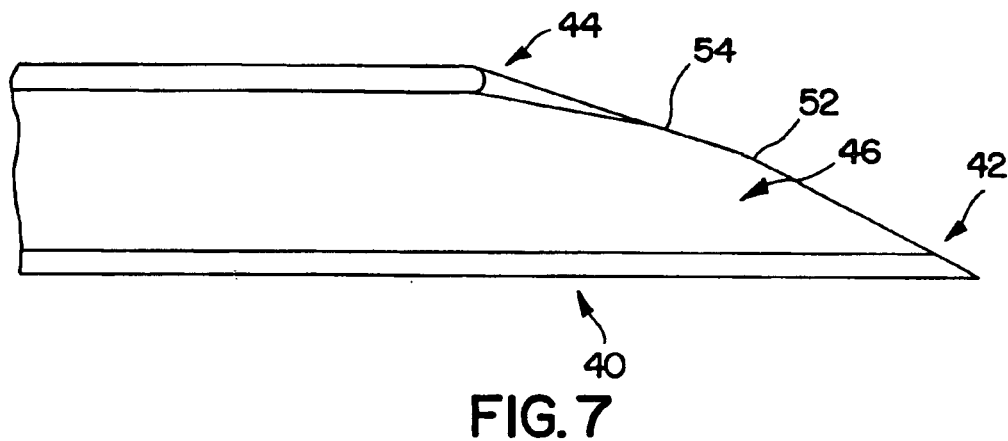
FIG. 7 is a side cross-sectional view of the cannula tip of FIG. 6.

As shown in FIG. 7, the trailing edge 44 of the cannula distal end is preferably fully radiused to prevent tissue from catching on this trailing edge during implant insertion. The radiused edge 44 also prevents coring of tissue by preventing a complete plug of tissue from being cut by the cannula. The radiused trailing edge 44 is blended out around the circumference of the cannula with the radiused portion completely blended out at a blend end 54 which is located within the central third of the cannula.

Figure 8:
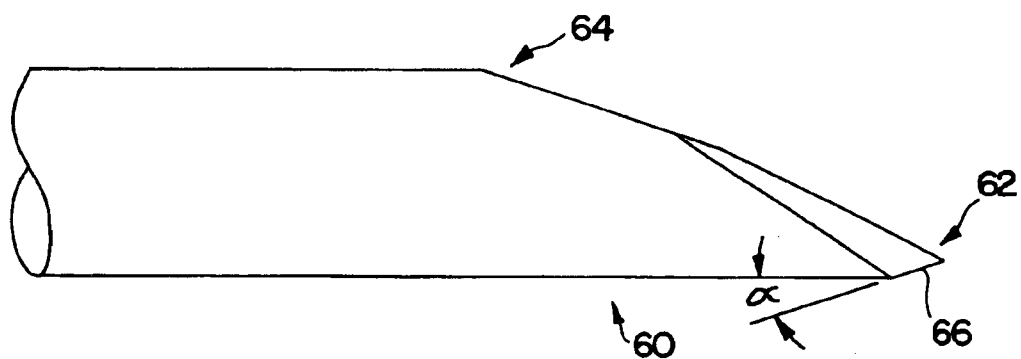
FIG. 8 is a side view of a cannula tip according to an alternative embodiment of the invention.
Figure 9:
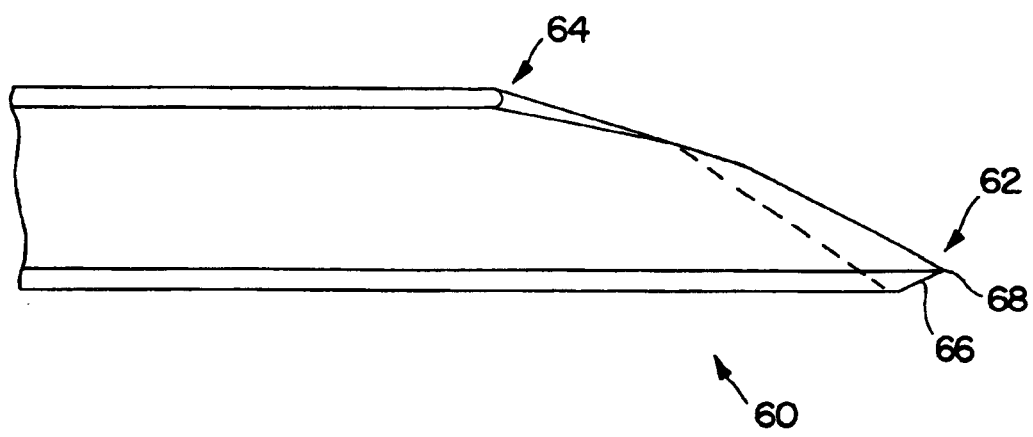
FIG. 9 is a side cross-sectional view of the cannula tip of FIG. 8.
Figure 11:
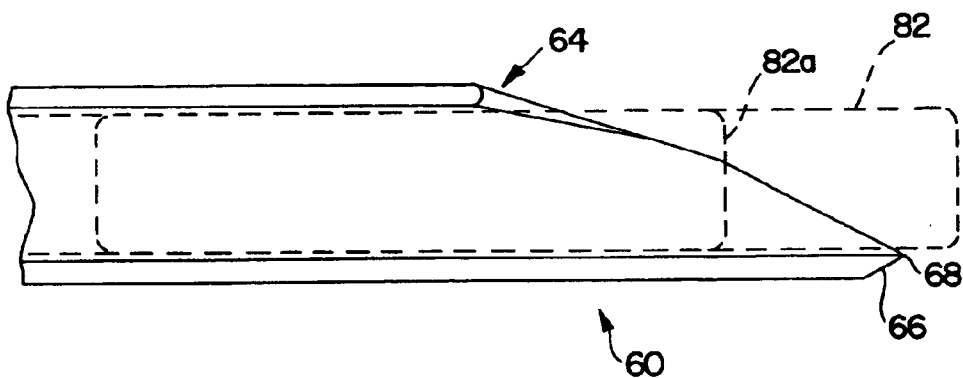
FIG. 11 is a side view of the cannula of FIG. 9 with an implant shown at two different positions inside the cannula.

FIGS. 8, 9, and 11 illustrate an alternative of a cannula tip 60 for use with the trocar according to the present invention. The cannula tip 60 has an angled distal end for inserting the cannula into tissue which includes a leading edge 62 and a trailing edge 64 of the cannula. As described above, the profile of the distal end includes an angle which is smaller near the trailing edge 64 than near the leading edge 62. This changing angle of the cannula tip profile helps to avoid tearing or coring of tissue during trocar insertion.

The cannula tip 60 is provided with a leading edge 62 having a reverse grind 66 around approximately one half of the circumference of the cannula. The reverse grind 66 is formed by a grinding operation which creates a beveled exterior surface of the cannula. The reverse grind 66 causes the leading cutting edge 68 of the cannula to be moved from the exterior diameter of the cannula to an interior diameter of the cannula. An angle $\alpha$ between the longitudinal axis of the cannula 60 and the surface of the reverse grind 66 is approximately 5 to 60 degrees, preferably 20 to 45 degrees. Although the reverse grind 66 is illustrated as having a planar cross-section, the grind may also have a slightly convex or concave cross-section.

Figure 10:
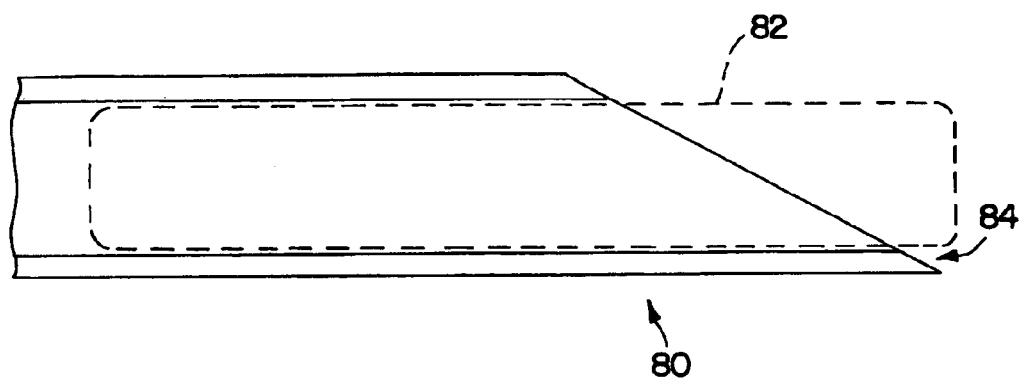
FIG. 10 is a side cross-sectional view of a prior art cannula tip with an implant inside the cannula.

One of the advantages of the reverse grind is illustrated by a comparison of FIGS. 10 and 11. In FIG. 10, a cannula 80 according to the prior art is illustrated with an implant 82 shown in hidden lines. If the implant 82 protrudes slightly from the cannula 80 during insertion, it can be seen that a gap 84 is present in which tissue can become trapped. This gap 84 of the prior art cannula increases the trauma and tearing of tissue due to trapping of tissue during implant insertion. However, with the reverse grind 66 shown in FIG. 11, the cannula leading cutting edge 68 having the reverse grind forces the tissue away from the implant 82 rather than into a gap between the implant and the cannula preventing tissue entrapment and possible implant jam.

Another advantage provided by the reverse grind 66 involves the improved cannula insertion due to the ability of the angled surface to push tissue apart during insertion. This angled or tapered surface of the reverse grind reduces tissue trauma and tearing. In addition, the reverse grind 66 improves tracking of the cannula. For example, a conventional cannula having an angle cut distal end as shown in FIG. 10 will track at an angle with respect to the axis of the cannula due to the angle distal end. However, the reverse grind 66 of the present invention provides a restoring force during cannula insertion which helps the cannula track along a substantially axial path.

FIG. 11 also illustrates a leading edge of an implant 82*a* positioned at a preferred position inside the cannula 60 for implantation. The implant 82*a* may be held at this position during implantation by the obturator or by another holding means. When the forward end of the implant 82*a* is positioned between the leading cutting edge 68 and the trailing edge 64 of the cannula as shown in FIG. 11 the implant edge will help to force the tissue apart reducing trauma and tearing of the tissue and preventing coring. According to a preferred implantation method, the implant 82*a* is positioned within the cannula with a forward end of the implant located between ⅓ and ⅔ of the way between the leading cutting edge 68 and the trailing edge 64.

The cannulas 20, 40, 60 according to the present invention may be formed of any of the known cannula materials such as plastic or metal. The retention trocar may be a single use device or may be reusable. The cannulas and trocars according to the present invention are intended for insertion of implants in animals including humans, livestock, and the like.

While the invention has been described in detail with reference to the preferred embodiments thereof, it will be apparent to one skilled in the art that various changes and modifications can be made, and equivalence employed, without departing from the spirit and scope of the invention.

What is claimed is:

1. A trocar comprising:
   a cannula for receiving an implant and inserting the implant into an animal, the cannula having a sharp tissue penetrating distal end;
   a spring element received entirely within the cannula, the spring element having a leaf spring for retaining the implant inside the cannula, the leaf spring applying a frictional force against the implant sufficient to prevent the implant from sliding out of the cannula under a weight of the implant, wherein the spring element is formed as a sheet with the leaf spring formed as a T-shaped cut out portion within the sheet; and
   an obturator for delivering the implant from the cannula into the animal.

2. The trocar according to claim 1, wherein the leaf spring has a longitudinal leg and cross leg, and the cross leg of the leaf spring is wider than the longitudinal leg in a circumferential direction.

3. The trocar according to claim 2, wherein the cross leg has tabs on either end which secure the leaf spring against motion away from a surface of the cannula towards an axis of the cannula.

4. The trocar according to claim 1, wherein the sheet is substantially rectangular.

5. A trocar comprising:
   a cannula for receiving an implant and inserting the implant into an animal;
   a spring element received within the cannula, the spring element having a leaf spring for retaining the implant inside the cannula, the leaf spring applying a frictional force against the implant sufficient to prevent the implant from sliding out of the cannula under a weight of the implant;
   an obturator for delivering the implant from the cannula into the animal; and
   wherein the leaf spring has a plurality of successive bends and the successive bends are arranged to alternatively contact an inside wall of the cannula and an outside of the implant to retain the implant in the cannula.

6. The trocar according to claim 5, wherein the leaf spring has a longitudinal leg arranged substantially parallel to an axis of the cannula and a cross leg substantially perpendicular to the longitudinal leg, and the plurality of successive bends are formed on the longitudinal leg.

7. The trocar according to claim 5, wherein the leaf spring having the plurality of successive bends is compressed in a radial direction of the cannula by insertion of the implant into the cannula.

8. The trocar according to claim 5, wherein the obturator has a tapered distal end to prevent ejection of the spring element from the cannula when the obturator is moved distally to eject the implant from the cannula.

9. The trocar according to claim 5, wherein the spring element is fixed within the cannula.

10. A trocar comprising:

a cannula for receiving an implant and inserting the implant into an animal;

a spring element received within the cannula, the spring element formed from a sheet with a continuous cut forming a T-shaped leaf spring connected to a surrounding sheet;

an obturator for delivering the implant from the carnula into the animal; and wherein the leaf spring retains the implant inside the cannula by applying a frictional force against the implant sufficient to prevent the implant from sliding out of the cannula under a weight of the implant.

11. The trocar according to claim 10, wherein the obturator has a tapered distal end to prevent ejection of the spring element from the cannula when the obturator is moved distally to eject the implant from the cannula 12. The trocar according to claim 10, wherein the spring element is fixed within the cannula.

13. The trocar according to claim 10, wherein the leaf spring is received entirely within the cannula.

14. The trocar according to claim 10, wherein the spring element is received entirely within the cannula.

15. The trocar according to claim 10, wherein the sheet is substantially rectangular.

* * * * *